United States Patent
Ball et al.

(10) Patent No.: US 7,172,598 B2
(45) Date of Patent: Feb. 6, 2007

(54) FORCE SPECIFIC IMPACTING DEVICE

(75) Inventors: Robert J. Ball, Winona Lake, IN (US); Jared Shoup, Tipp City, OH (US)

(73) Assignee: DePuy Products, Inc., Warsaw, IN (US)

( * ) Notice: Subject to any disclaimer, the term of this patent is extended or adjusted under 35 U.S.C. 154(b) by 306 days.

(21) Appl. No.: 10/260,983

(22) Filed: Sep. 30, 2002

(65) Prior Publication Data

US 2004/0064145 A1    Apr. 1, 2004

(51) Int. Cl.
*A61B 17/58* (2006.01)
*A61F 2/00* (2006.01)

(52) U.S. Cl. ............................................. 606/99

(58) Field of Classification Search ............ 606/53, 606/86, 91, 99, 100; 433/25, 141, 150, 151, 433/2, 5, 18, 118, 121; 81/463, 20–27, 177.1, 81/177.4; 173/90, 91, 112, 202, 128, 210; 29/242, 243, 278, 270, 254, 255, 275; 269/3, 269/6; 100/240, 245, 251, 219, 229 A, 229 R, 100/260; 401/246, 247, 243, 202; 403/DIG. 11, 403/263

See application file for complete search history.

(56) References Cited

U.S. PATENT DOCUMENTS

| | | | | | |
|---|---|---|---|---|---|
| 1,084,766 | A | * | 1/1914 | Thomas | 433/151 |
| 1,837,067 | A | * | 12/1931 | Reiter | 606/84 |
| 2,376,187 | A | * | 5/1945 | Reiter | 433/151 |
| 2,480,366 | A | * | 8/1949 | Hewitt | 29/221.5 |
| 2,725,878 | A | | 12/1955 | Reiter | |
| 3,036,482 | A | * | 5/1962 | Kenworthy et al. | 173/90 |
| 3,147,484 | A | * | 9/1964 | Permil | 227/139 |
| 3,210,836 | A | * | 10/1965 | Johanson et al. | 29/278 |
| 4,394,097 | A | * | 7/1983 | Horlacher | 403/360 |
| 4,439,184 | A | * | 3/1984 | Wheeler | 604/90 |
| 4,583,652 | A | * | 4/1986 | Goldberg | 215/256 |
| 4,703,549 | A | * | 11/1987 | Grandt | 29/426.5 |
| 5,102,421 | A | | 4/1992 | Anspach, Jr. | |
| 5,127,754 | A | * | 7/1992 | Mase | 401/202 |
| 5,186,564 | A | * | 2/1993 | Fuhrmann et al. | 401/202 |
| 5,282,805 | A | | 2/1994 | Richelsoph et al. | |
| 5,486,181 | A | | 1/1996 | Cohen et al. | |
| 5,620,445 | A | | 4/1997 | Brosnahan et al. | |

(Continued)

FOREIGN PATENT DOCUMENTS

EP    0549362    6/1993

(Continued)

*Primary Examiner*—Eduardo C. Robert
*Assistant Examiner*—Ahu Ramana
(74) *Attorney, Agent, or Firm*—Maginot, Moore & Beck

(57) ABSTRACT

An impacting device includes a hollow body and a movable member. The hollow body includes an inner chamber having an interior surface, the interior surface including at least one interference member extending radially inward therefrom. The hollow body also includes an impact surface at one end thereof. The movable member has a proximal impacting surface and is at least partly disposed within the hollow body. The movable member is movable with respect to the hollow body, and includes at least on interfering member configured to engage the at least one interference member of the hollow body The movable member is operable to move the interfering member past the interference member responsive to at least a first impacting force applied the proximal impacting surface

21 Claims, 6 Drawing Sheets

U.S. PATENT DOCUMENTS

| | | | |
|---|---|---|---|
| 5,628,105 A * | 5/1997 | Fallandy et al. | 29/566.4 |
| 5,800,546 A | 9/1998 | Marik et al. | |
| 5,919,196 A | 7/1999 | Bobic et al. | |
| 5,980,528 A | 11/1999 | Salys | |
| 6,010,508 A | 1/2000 | Bradley | |
| 6,022,355 A | 2/2000 | Péche et al. | |
| 6,165,177 A | 12/2000 | Wilson et al. | |
| 6,238,435 B1 | 5/2001 | Meulink et al. | |
| 6,240,811 B1 * | 6/2001 | Oesterle et al. | 81/90.2 |
| 6,270,502 B1 | 8/2001 | Stulberg | |
| 6,349,618 B1 * | 2/2002 | Lowther | 81/27 |
| 2002/0014558 A1 | 2/2002 | Holemans | |

FOREIGN PATENT DOCUMENTS

| | | | |
|---|---|---|---|
| EP | 0582849 | | 2/1994 |
| EP | 1004284 | | 5/2000 |
| EP | 1190687 | | 3/2002 |
| JP | 11078359 | * | 3/1999 |

* cited by examiner

FORCE SPECIFIC IMPACTING DEVICE

FIELD OF THE INVENTION

The present invention relates to impacting devices, such as those used to provide impact force to a prosthetic component in order to secure the prosthetic component to another device or to tissue.

BACKGROUND OF THE INVENTION

Many orthopaedic procedures involve the implantation of prosthetic devices to replace badly damaged or diseased bone tissue Common orthopaedic procedures that involve prosthetic devices include total or partial hip, knee and shoulder replacement. For example, a hip replacement often involves a prosthetic femoral implant. The femoral implant usually includes a rigid stem that is secured within the natural femur bone tissue. The femoral implant further includes a rounded head that is received by, and may pivot within, a natural or artificial hip socket. Shoulder replacement is somewhat similar, and typically includes a humeral implant that includes a rigid stem and a rounded head. The rigid stem is secured within the natural humerus bone tissue and the rounded head is pivotally received by a shoulder socket Increasingly, prosthetic devices are provided as subcomponents that are assembled during surgery. In particular, the different anatomies of different patients require that prosthetic devices such as femoral and humeral implants be available in different sizes and configurations. By way of simplified example, a humeral implant may be available in as many as six or more humeral head diameters. Stems may similarly vary in size and/or in shape. Because the appropriate overall configuration of the implant can typically only be determined during the surgical procedure, it is advantageous that the surgeon have at her disposal many configurations and sizes of implants. Instead of providing a separate implant for each possible combination of features, implants are provided as modular kits of subcomponents that allow the surgeon mix and match different subcomponents to achieve the most advantageous combination for the patient. Thus, the surgeon can pick from several sizes or configurations of each component and combine the components to form an implant having an optimal combination of features.

One example of a modular implant is the humeral implant 10 shown in FIG. 1. The humeral implant 10 includes a humeral head 12 that may be assembled onto a humeral stem 14. The humeral stem 14 is configured to be implanted in the intramedullary tissue of a natural humeral bone, while the humeral head 12 is configured to be received into the shoulder socket or glenoid cavity. The humeral head 12 includes a tapered plug 16 that is designed to be received by a tapered receptable 18 in the humeral stem 14 It can be appreciated that the surgeon may secure alternative humeral head designs on the same humeral stem 14, thus providing the surgeon with a broad array of humeral head size options.

Once the components are selected, such as the humeral head 12 and the humeral stem 14 of FIG. 1, then the components are assembled either externally or in vivo. A popular method of securing implant components together involves the use of a Morse taper. The components of FIG. 1 by way of example include a Morse taper arrangement. In particular, a Morse taper is a feature in which a tapered male component, e.g. the tapered plug 16, is received into a tapered female component, e.g. the receptacle 18. The taper angle of the plug 16 is preferably, but need not be, slightly less than the taper angle of the receptacle 18. In use, the plug 16 advances into the receptacle 18 until it begins to engage the receptacle 18. The further into the receptacle the plug 16 is forced, the more tightly it engages.

The force applied to secure the plug 16 within the receptacle 18 is proportional to the retention force of the plug 16 within the receptacle 18. Thus, if a sufficient amount of force is applied, then the humeral head 12 will be securely fastened in the humeral stem 14. Other prosthetic devices employ Morse tapers for substantially the same reasons.

To apply sufficient force to lock the Morse taper arrangement, it is known to impact the humeral head 12 such that the impact force directs the humeral head 12 toward the humeral stem 14. The impact force drives the plug 16 into the receptacle 18 and forms the Morse taper lock A hammer or mallet is typically struck directly on the head, or through an impacting plate, tool or mechanism.

Previously, the surgeon (or other person) would impact a prosthetic implant several times without knowing if sufficient force had been applied to lock the Morse taper sufficiently. Often, in order to be sure that the Morse taper had locked, the surgeon or assistant would use excess force. The use of excess force is undesirable because of the potential for damage to the bone tissue or implant device.

Thus, there is a need for assisting surgical personnel in determining whether sufficient force has been applied to a Morse taper to lock the Morse taper. Such need is widespread as Morse tapers have commonly been used for connection of many types of implant devices.

SUMMARY OF THE INVENTION

The present invention provides the above needs, as well as others, by providing a force specific impacting tool. In particular, the impacting tool of the present invention includes two elements that require a first amount of force to overcome an interference between the two elements. If the interfering features and/or the other structures of the tool are chosen such that the first amount of force corresponds to amount of force to lock a Morse taper, then a surgeon may use the impact tool to impact a device having a Morse taper and be assured that sufficient force has been applied when the interference between the two elements is overcome.

A first embodiment of the invention is an impacting device that includes a hollow body and a movable member. The hollow body includes an inner chamber having an interior surface, the interior surface including at least one interference member extending radially inward therefrom. The hollow body also includes an impact surface at one end thereof. The movable member has a proximal impacting surface and is at least partly disposed within the hollow body. The movable member is movable with respect to the hollow body, and includes at least on interfering member configured to engage the at least one interference member of the hollow body. The movable member is operable to move the interfering member past the interference member responsive to at least a first impacting force applied the proximal impacting surface.

A second embodiment of the invention is a method that includes placing an impact surface of a hollow body on the prosthetic device, the hollow body including an inner chamber having an interior surface, the interior surface including at least one interference member extending radially inward therefrom The method also includes disposing at least one interfering member of a movable member within the inner chamber and against the at least one interference member of the hollow body such that engagement of the at least one interference member and the at least one interfering member inhibits movement of the movable member in a first direction. The method further includes impacting a proximal impacting surface of the movable member with a sufficient force to cause the at least one interfering member to move past the at least one interference member in the first direction.

The above embodiments may be used to ensure that sufficient force has been applied to lock a Morse taper arrangement. As such, the above embodiments provide the advantage of reducing the tendency to use unnecessary excessive force. Moreover, the above embodiments may be implemented relatively simply and inexpensively The force specific impact tool and method may further be used for other surgical purpose in which impact force is advantageously limited, such as for implanting a device within bone tissue, or for assembling components that employ non-Morse taper connecting features The above described features and advantages, as well as others, will become more readily apparent to those of ordinary skill in the art by reference to the following detailed description and accompanying drawings.

DETAILED DESCRIPTION

Figure 2:
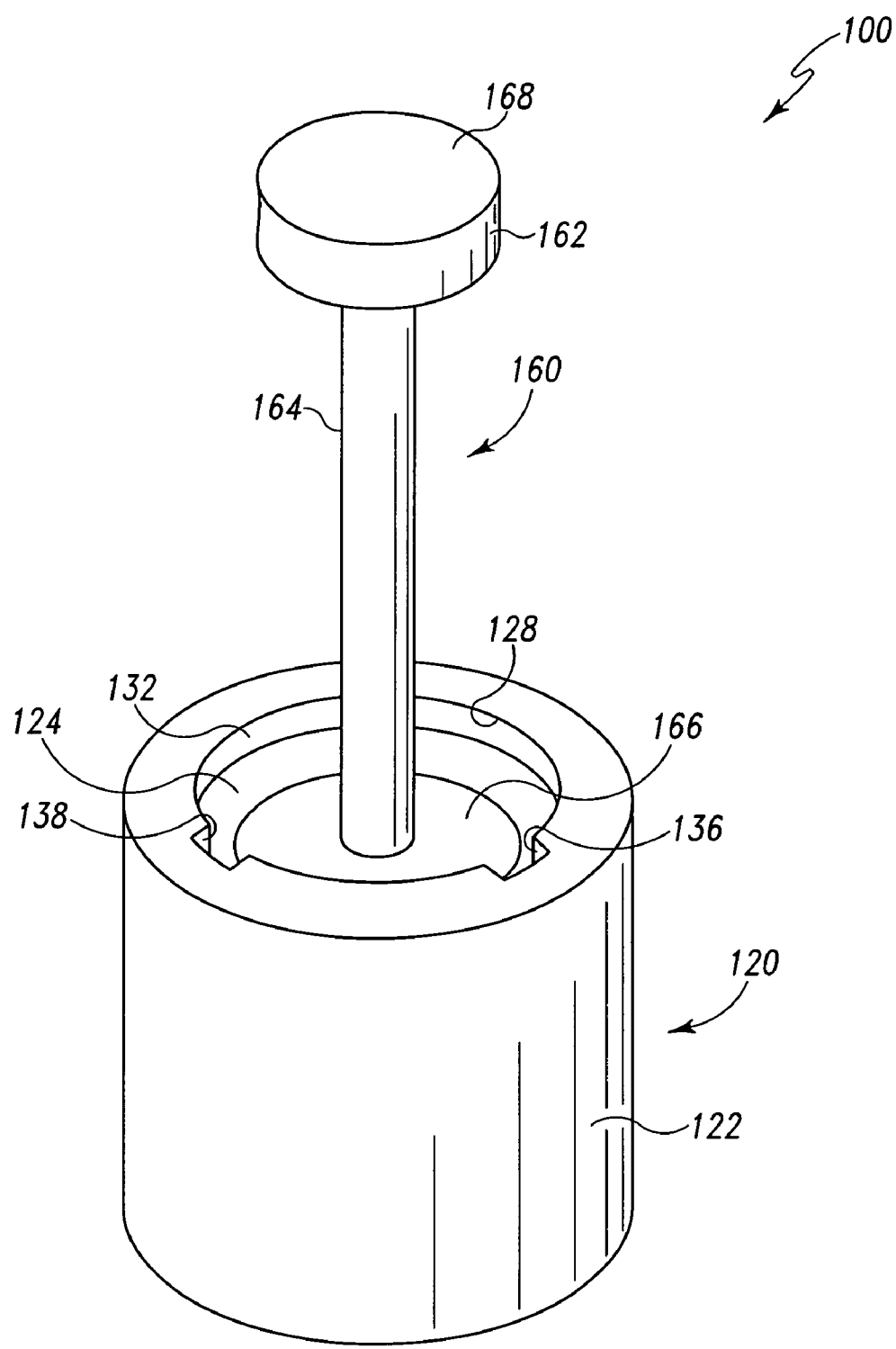
FIG. 2 shows a perspective view of an exemplary impacting tool according to the present invention.
Figure 4:
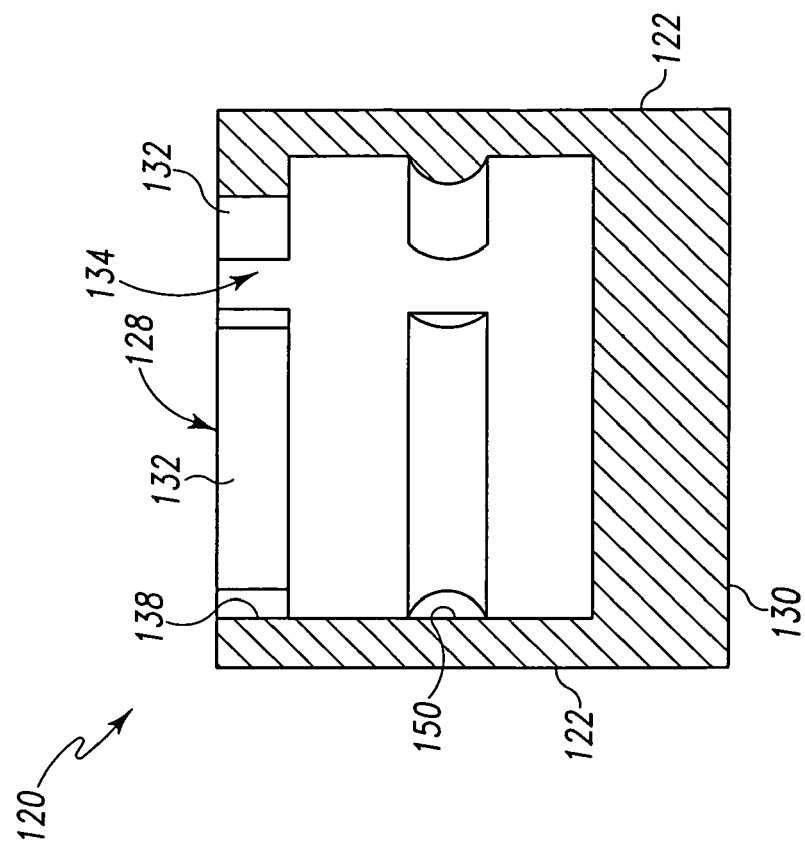
FIG. 4 shows a cutaway view the hollow body taken along line IV—IV of FIG. 3.
Figure 3:
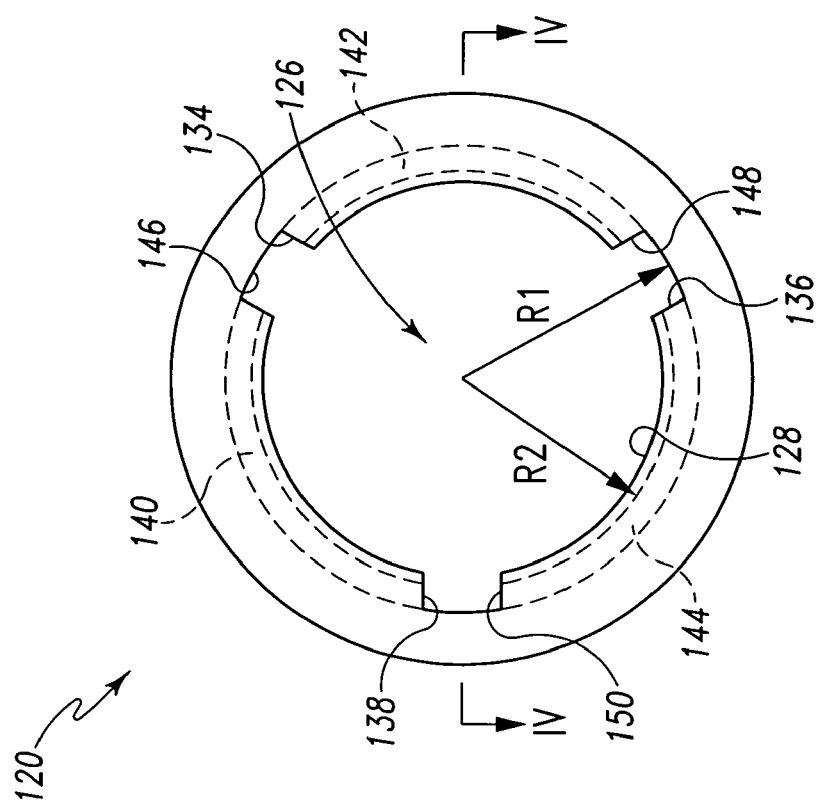
FIG. 3 shows a top view of the hollow body of the impacting tool of FIG. 2.
Figure 6:
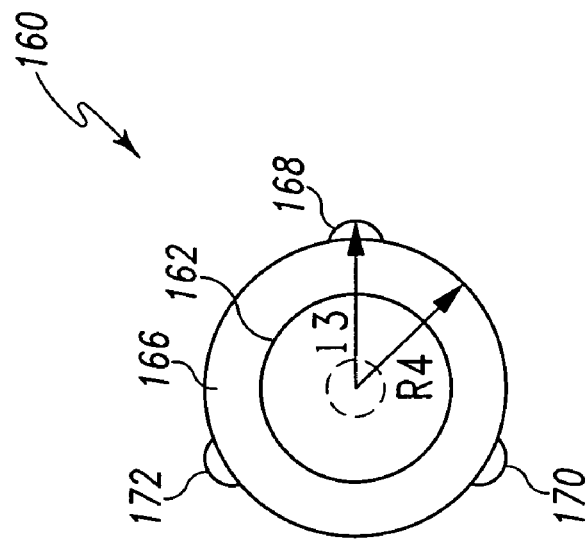
FIG. 6 shows a top plan view of the movable member of FIG. 5.
Figure 5:
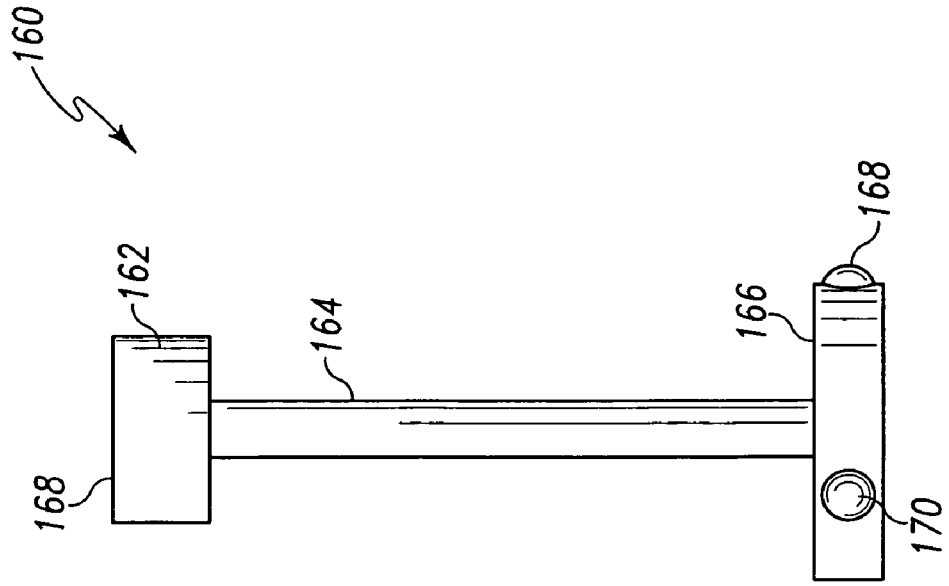
FIG. 5 shows a side plan view of the movable member of the impacting tool of FIG. 2.

FIG. 2 shows an exemplary embodiment of an impacting tool 100 according to the present invention. The impacting tool 100 generally comprises an impacting member in the form of a hollow body 120 and a force translation member in the form of a movable member 160. FIGS. 3 and 4 show different views of the hollow body 120 apart from the movable member 160, and FIGS. 5 and 6 show different views of the movable member 160 apart from the hollow body 120. The drawing figures will be reference contemporaneously in the following detailed descriptions. Like reference numbers are used to identify like features throughout The hollow body 120 in the exemplary embodiment described herein is a generally open-ended cylinder that includes an exterior surface 122 and an interior surface 124 defining an inner chamber 126. The hollow body 120 includes an opening 128 at one end and an impact surface 130 at the other end An annular lip 132 defines the periphery of the opening 128 and has a radius that is slightly smaller than a radius R1 of the interior surface 124, thereby defining the "lip". The annular lip 132 includes three voids 134, 136 and 138 configured to receive corresponding protrusions 168, 170 and 172 on the movable member 160 when the protrusions 168, 170 and 172 are aligned with the voids 134, 136 and 138.

Within the inner chamber 126, the hollow body 120 includes a plurality of interference features 140, 142 and 144 that extend radially inward from the interior surface 124. In the exemplary embodiment, the interference features 140, 142 and 144 are in the form of protrusions that extend partly around the circumference of the interior surface 124. The protrusions 140, 142 and 144 are spaced apart such that, as a group, they form broken annular rib having three voids 146, 148 and 150 that correspond to the protrusions 168, 170 and 172 on the movable member 160. In the exemplary embodiment described herein, the protrusions 140, 142, and 144 have an arcuate or convex cross section, as exemplified by the edge 140a of the protrusion 140 in FIG. 4.

The protrusions 140, 142 and 144 are disposed approximately midway within the inner chamber 126.

The movable member 160 in the exemplary embodiment described herein includes a proximal impacting plate 162, a translation element 164 and a support disk 166 The impacting plate 162 may suitably be any shape, but should have a relatively large top surface 168 sufficient to conveniently receive the impact of a mallet or other pounding instrument. The translation element 164 may suitably be any elongate and rigid rod, tube, or block that freely moves through the opening 128.

The support disk 166 is in the form of a circular disk that includes a plurality of protrusions 168, 170 and 172 extending radially outward therefrom. The protrusions 168, 170 and 172 in the exemplary embodiment described herein are hemispherical in shape. The support disk 166 has a radius R3 that is less than a radius R2 of the broken annular rib defined by the protrusions 140, 142 and 144 of the hollow body 120. However, a radius R4 defined from the axis of the support disk 166 to the outermost part of the any of the protrusions 168, 170 and 172 exceeds the radius R2 The radius R4 is less than, however, a radius R1 of the interior surface 124 of the inner chamber 126. As a consequence, movement of the support disk 166 is not significantly impeded by the interior surface 124.

Figure 7:
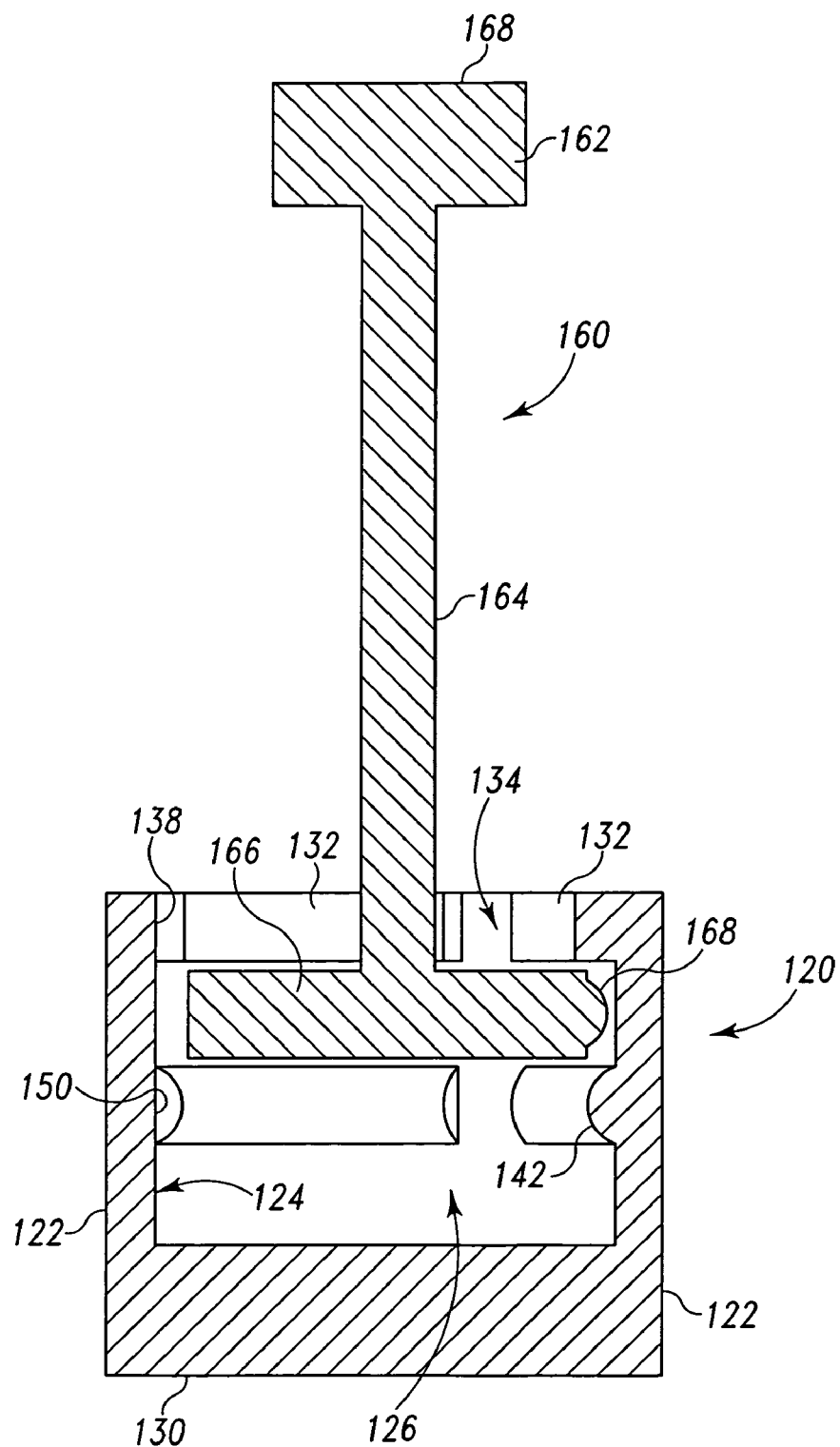
FIG. 7 shows the impacting tool of FIG. 2 prior to impact.

In operation, the support disk 166 of the movable member 160 is first disposed within the inner chamber 126 above the protrusions 140, 142 and 144 (see FIG. 7). To this end, the movable member 160 is rotated to a position in which the protrusions 168, 170 and 172 align with the voids 134, 136 and 138. The movable member 160 is then moved axially inward such that the protrusions 168, 170 and 172 pass through the voids 134, 136 and 138 and into the inner chamber 126 above the protrusion 140, 142 and 144. The movable member 160 is then rotated again, if necessary, until the protrusions 168, 170 and 172 do not align with the voids 146, 148 and 150.

In such position, the protrusions 140, 142 and 144 impede further inward axial movement of the support disk 166 by engaging or interfering with the protrusions 168, 170 and 172 (see FIG. 7). In addition, the annular lip 132 helps retain the support disk 166 within the inner chamber 126 To this end, the annular lip 132, which has a nominal radius that is less than R3, will engage the protrusions 168, 170 and 172 to impede axially outward movement of the disk 166 so long as the protrusions 168, 170 and 172 are not aligned with the voids 134, 136 and 138. Preferably, the voids 134, 136 and 138 are aligned with the voids 146, 148 and 150 such that any time the movable member 160 is rotated into the position in which the protrusions 140, 142 and 144 inhibit axially inward movement of the disk 166, the annular lip 132 will also inhibit axially outward movement of the disk 166. In this manner, the assembled impact tool 100 may be readily manipulated with one hand without significant risk of disengagement of the movable member 160 from the hollow body 120.

Figure 8:
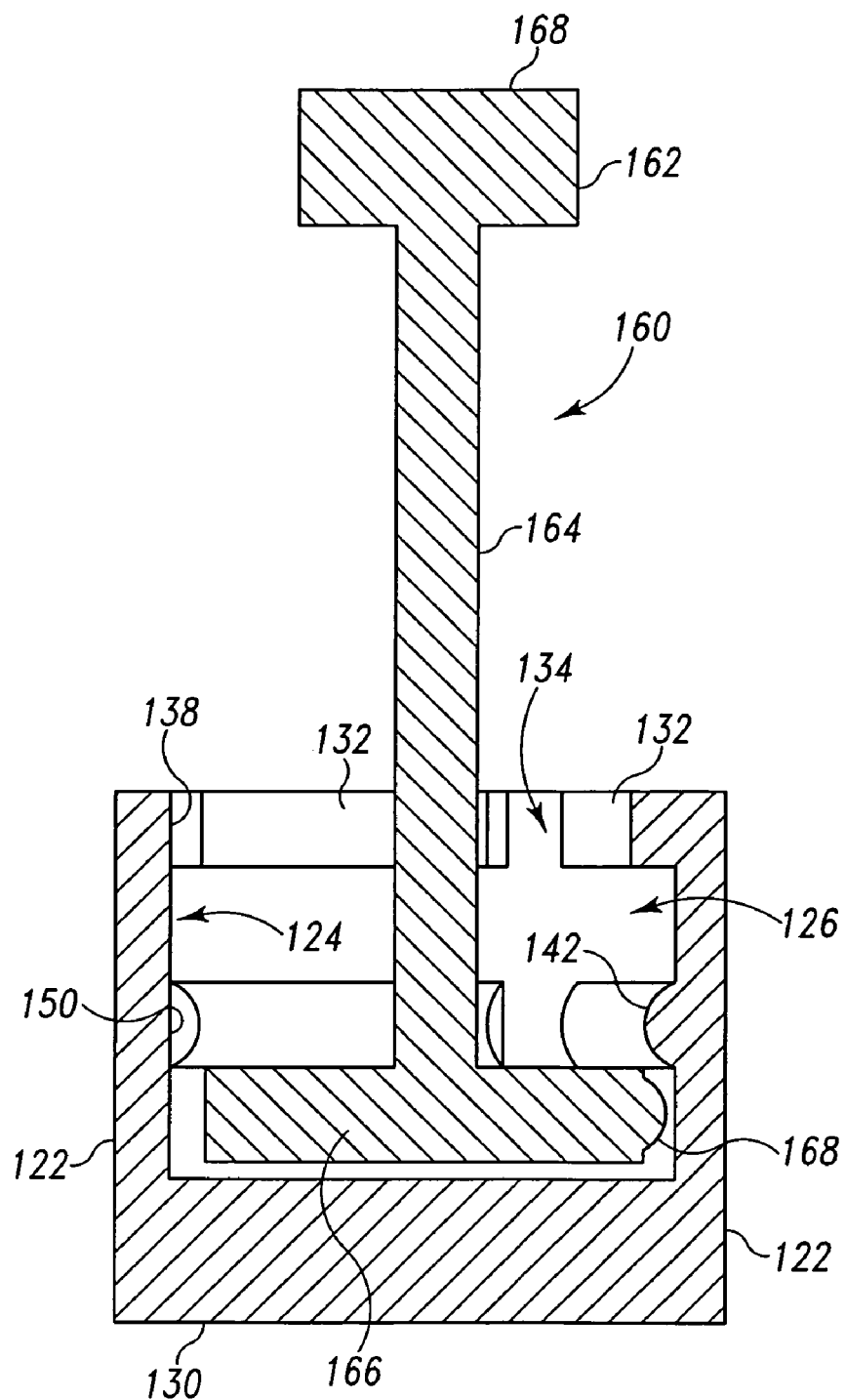
FIG. 8 shows the impacting tool of FIG. 2 after impact.

Once the disk 166 is located within the inner chamber 126 and the protrusions 140, 142 and 144 are engaging the protrusions 168, 170 and 172 to inhibit axial movement of the disk 166, the impact surface 130 is placed over a device to be impacted such as an implant device having a Morse taper feature. For example, the impact surface 130 may be placed on top of the humeral head 12 of FIG. 1. The surgeon then impacts the proximal impacting plate 162 with a mallet or other impacting device, not shown. The surgeon impacts the plate 162 until the force of the impacting causes the protrusions 168, 170 and 172 to overcome the interference from the protrusions 140, 142 and 144 and the disk 166 moves below the protrusions 140, 142 and 144 (see FIG. 8). The force that overcomes the interference is translated to the impact surface 130, which then translates the force to the implant. The amount of force required to overcome the interference preferably corresponds to the amount of force required to ensure the Morse taper lock.

To this end, the interfering members of the movable member 160 and the hollow body 120 must be configured in such a manner that it requires (roughly) a predetermined amount of force to overcome the interference. As a result, the surgeon has confirmation that a sufficient amount of impact force has been applied to the implant device to lock the Morse taper when the interference has been overcome. This confirmation reduces the tendency of the surgeon to excessively impact the implant device.

The amount of force required to overcome the interference of the protrusions 168, 170 and 172 with the protrusions 140, 142 and 144 depends upon a number of parameters. One parameter is the choice of materials, and in particular, the hardness/elasticity of the materials, from which the hollow body 120 and the disk 166 are constructed. Other parameters include the difference between the radii R3 and R2. In particular, one may reduce the amount of force required by reducing the difference between the radii R3 and R2 Contrariwise, one may increase the amount of force required by increasing the difference between the radii R3 and R2 The cross sectional shapes of the protrusions 168, 170 and 172 and/or the protrusions 140, 142 and 144 may also be altered to change the required amount of force.

The proper selection of the above described parameters to achieve a given amount of force may be done theoretically, empirically though trial and error, or a combination of both. In a preferred embodiment in which the impacting tool 100 is "tuned" or configured for use with a particular Morse taper feature, the parameters of the impact tool 100 are chosen such that the amount of force required to overcome the interference between the protrusions 168, 170 and 172 and the protrusions 140, 142 and 144 exceeds the amount of force required by to sufficient lock the Morse taper feature It will be appreciated that the above describe embodiment is merely exemplary and that those of ordinary skill in the art may readily devise their own implementations and embodiments that incorporate the principles of the present invention and fall within the spirit and scope thereof.

To this end, it will be appreciated that other numbers and types of interfering features may be used instead of the protrusions 140, 142, 144, 168, 170, and 172 For example, the protrusions 168, 170 and 172 may take many shapes, and need not be hemispherical. By way of nonlimiting example, the protrusions 168, 170 and 172 may take the general shape of arcuate members similar to the protrusions 140, 142 and 144 shown in FIGS. 3 and 4 Those of ordinary skill in the art would readily recognize that nearly any shape of protrusion may be used. Similarly, the protrusions 140, 142 and 144 may take many shapes. For example, instead of using protrusions that are flat in the circumferential direction, the protrusions may form other shapes, such as a U-shape or V-shape in the circumferential direction that serves to "catch" the protrusions 168, 170 and 172 of the disk 166.

Moreover, it will be readily appreciated that alternative configurations of members other than the hollow body 120 and movable member 160 are capable of including interfering elements that inhibit movement until a first impact force is received Such alternative embodiments would provide at least some of the advantages of the invention described herein. For example, it can readily be seen that even the impact device 100 can be reversed, such that the hollow body 120 (or similar design) receives the impact from the surgeon and the movable member 160 (or similar design) imparts the force to the implant device.

In addition, the inner surface 124 of the hollow body 120 may suitably have a non-circular cross section, for example, a rectangular, square, triangular, polygonal or elliptical cross section. While such a device could have the disadvantage of being more difficult to reset after use, it could nevertheless still assist a surgeon in applying a minimal amount of force necessary to ensure a connection between prosthetic components In such alternatives, the disk 166 could still be used. In addition, it will be appreciated that the cross-section of the exterior surface of the hollow body 120 may be other shapes without significantly affecting the utility of the tool, although other designs could be more or less ergonomic.

Figure 1:
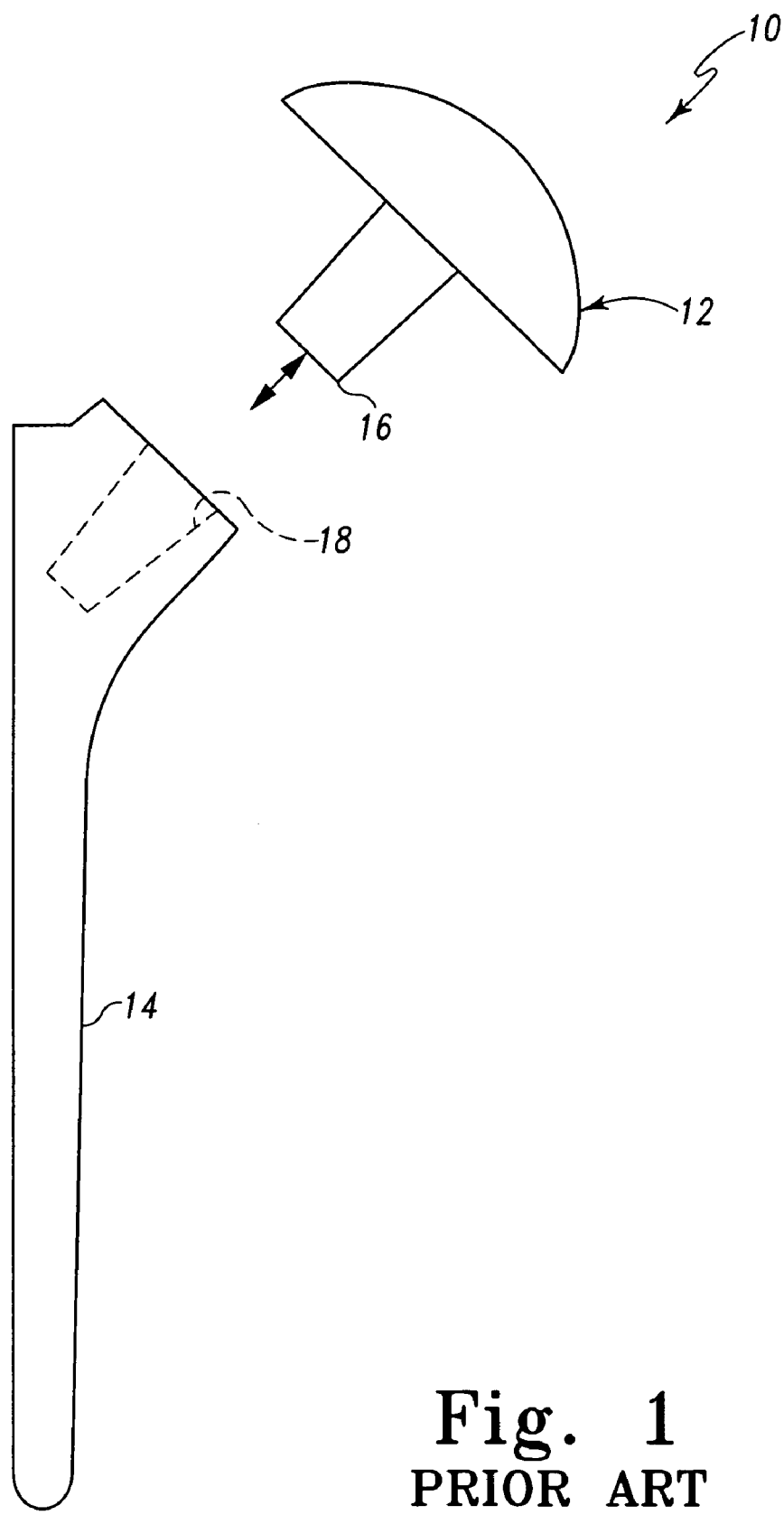
FIG. 1 shows a side plan view of a prior humeral implant that employs a Morse taper.

In addition, it will be appreciated that the hollow body 120 (or other device that engages the implant) may be connected to, or outfitted with, a mechanism that grasps the implant, such as around the head 12 of the implant 10 of FIG. 1. Such a mechanism could assist the surgeon in holding the impacting device 100 in place prior to impact. Moreover, such a grasping mechanism could be used for testing the integrity of the implant assembly after the impacting step. For example, the lip 132 may function as an interfering member that is configured to inhibit movement of the disk 166 out of the inner chamber 126 unless a predetermined second outward force is applied. The amount of force required to overcome the lip 132 would preferably be less than the force required to overcome the protrusions 140, 142 and 144. As such, if desired, the surgeon may apply an upward force to the impacting plate 162 of the movable member 160 while the impact tool 100 is grasping the implant head in an exercise that helps confirm to the surgeon that the implant is securely assembled Because the force required to overcome the lip 132 is less than that require to overcome the protrusions 140, 142 and 144, the disk 166 should exit the lip 132 before the implant is disassembled. Such an exercise would confirm to the surgeon that the implant has been adequately secured together.

We claim:
1. An impacting device comprising:
   a hollow body, the hollow body including an inner chamber having an interior surface, the interior surface including at least one interference member extending radially inward therefrom, the hollow body further comprising an impact surface at one end thereof;
   a movable member having a proximal impacting surface, at least a part of the movable member disposed within the hollow body, the movable member being movable with respect to the hollow body, the movable member further including at least one interfering member configured to engage the at least one interference member of the hollow body;
wherein the movable member is operable to move the interfering member past the interference member responsive to at least a first impacting force applied to the proximal impacting surface, the movable member operable to translate at least a portion of the first impacting force to the impact surface of the hollow body, and
wherein the movable member is rotatable with respect to the hollow body, and wherein the interfering member and the interference member engage when the movable member is in a first rotational position with respect to the hollow body, and wherein the interfering member and the interference member do not engage when the movable member is in a second rotation position.

2. The impacting device of claim 1 wherein the interior surface is at least partly cylindrical.

3. The impacting device of claim 1 wherein the interfering member and the interference member are configured such that the first impact force corresponds to an amount of force required to lock a Morse taper through impaction by the impact surface.

4. An impacting device comprising:
a hollow body, the hollow body including an inner chamber having an interior surface, the interior surface including at least one interference member extending radially inward therefrom, the hollow body further comprising an impact surface at one end thereof;
a movable member having a proximal impacting surface, at least a part of the movable member disposed within the hollow body, the movable member being movable with respect to the hollow body, the movable member further including at least one interfering member configured to engage the at least one interference member of the hollow body;
wherein the movable member is operable to move the interfering member past the interference member responsive to at least a first impacting force applied to the proximal impacting surface, the movable member operable to translate at least a portion of the first impacting force to the impact surface of the hollow body, and
wherein the movable member includes a disk disposed within the hollow body, the at least one interfering member extending radially from the disk.

5. The impacting device of claim 4 wherein the hollow body includes an open top having a lip formed therein, the lip having a radius that is greater than a radius of the disk and configured to engage the at least one interfering member, the lip including at least one slot for receiving the at least one interfering member when the at least one interfering member is aligned with the at least one slot.

6. An impacting device comprising:
a hollow body, the hollow body including an inner chamber having an interior surface, the interior surface including at least one interference member extending radially inward therefrom, the hollow body further comprising an impact surface at one end thereof;
a movable member having a proximal impacting surface, at least a part of the movable member disposed within the hollow body, the movable member being movable with respect to the hollow body, the movable member further including at least one interfering member configured to engage the at least one interference member of the hollow body;
wherein the movable member is operable to move the interfering member past the interference member responsive to at least a first impacting force applied to the proximal impacting surface, the movable member operable to translate at least a portion of the first impacting force to the impact surface of the hollow body,
wherein the at least one interference member comprises a plurality of spaced-apart protrusions that together form a broken annular rib, and
wherein the at least one interfering member comprises a plurality of protrusions extending radially outward from a support disk.

7. An impacting device comprising:
a hollow body, the hollow body including an inner chamber having an interior surface, the interior surface including at least one interference member extending radially inward therefrom, the hollow body further comprising an impact surface at one end thereof;
a movable member having a proximal impacting surface, at least a part of the movable member disposed within the hollow body, the movable member being movable with respect to the hollow body, the movable member further including at least one interfering member configured to engage the at least one interference member of the hollow body;
wherein the movable member is operable to move the interfering member past the interference member responsive to at least a first impacting force applied to the proximal impacting surface, the movable member operable to translate at least a portion of the first impacting force to the impact surface of the hollow body, and
wherein the at least one interfering member comprises a plurality of protrusions extending radially outward from a support disk.

8. A method of impacting a prosthetic device, comprising:
a) placing an impact surface of a hollow body on the prosthetic device, the hollow body including an inner chamber having an interior surface, the interior surface including at least one interference member extending radially inward therefrom;
b) disposing at least one interfering member of a movable member within the inner chamber and against the at least one interference member of the hollow body such that engagement of the at least one interference member and the at least one interfering member inhibits movement of the movable member in a first direction; and
c) impacting a proximal impacting surface of the movable member with a sufficient force to cause the at least one interfering member to move past the at least one interference member in the first direction.

9. The method of claim 8 wherein b) further comprises:
aligning the at least one interfering member of the movable member with at least one void defined in a lip of the hollow body when the at least one interfering member is disposed outside of the inner chamber; and
moving the at least one interfering member through the at least one void until the at least one interfering member is disposed within the inner chamber.

10. The method of claim 9 further comprising:
d) aligning the movable member such that at least one interference member does not interfere with movement in a second direction opposite the first direction; and
e) moving the at least one interfering member past the at least one interference member in the second direction.

11. The method of claim 8 further comprising:
d) aligning the movable member such that at least one interference member does not interfere with movement in a second direction opposite the first direction; and
e) moving the at least one interfering member past the at least one interference member in the second direction.

12. The method of claim 8 wherein the at least one interference member comprises a plurality of spaced-apart protrusions.

13. The method of claim 8 wherein the at least one interference member comprises a plurality of spaced-apart protrusions that together form a broken annular rib.

14. The method of claim 8 wherein the at least one interfering member comprises a plurality of protrusions extending radially outward from a support disk.

15. An impacting device comprising an impacting member and a force translation member configured to movably couple to at least a portion of the impacting member, the force translation member having an impacting surface for receiving an impact force and a first interference member, the impacting device including a second interference member, and wherein engagement of the first interference member and the second interference member inhibits relative movement of the force translation member and the impacting member in a first direction, the first interference member and the second interference member configured to allow relative movement in the first direction responsive to an first impact force received at the impacting surface,
wherein the first interference member and the second interference member are configured to allow relative movement in the first direction responsive to an first impact force received at the impacting surface when the force translation member and the impacting member are in a first relative rotational position; and
wherein the first interference member and the second interference member are configured to allow relative movement in the first direction responsive to a force less than the impact force when the force translation member and the impacting member are in a second relative rotational position.

16. The impacting device of claim 15 wherein one of the impacting member and the force translation member has an inner chamber for receiving at least a portion of the other of the impacting member and the force translation member.

17. The impacting device of claim 16 wherein said inner chamber has an inner surface, the inner surface having a circular cross section.

18. A method comprising:
providing (i) an impacting member with an impact surface operably connected to an interference member to transfer force from the interference member to the impact surface; and (ii) a force translation member with an impacting surface operably connected to an interfering member to transfer force from the impacting surface to the interfering member, wherein the interference member and the interfering member are configured to transfer a first impact force from the interfering member to the interference member, and are operable to transfer only a portion of a second impact force from the interfering member to the interference member, the second impact force being greater than the first impact force;
providing a prosthetic device including (i) a first prosthetic component having a first Morse taper coupling feature, and (ii) a second prosthetic component having a second Morse taper coupling feature;
positioning the impact surface of the impacting member on the first prosthetic component while the first Morse taper coupling feature and the second Morse taper coupling feature are in mating relationship; and
impacting the impacting surface of the translation member with an object after the positioning step so as to cause the first Morse taper coupling feature and the second Morse taper coupling feature to become locked together.

19. The method of claim 18, wherein:
the impacting member comprises an outer wall extending from the impact surface and defining a compartment;
the interference member comprises a first protuberance extending into the compartment;
the interfering member comprises a second protuberance extending from the force translation member and configured to engage the interference member, and
the impacting step includes advancing the second protuberance toward the first protuberance so that the second protuberance contacts the first protuberance.

20. The method of claim 19, wherein:
at least one of the first protuberance of the interference member and the second protuberance of the interfering member comprises a resilient material; and
the interference member and the interfering member are configured such that when the first impact force is applied to the impacting surface and the interference member and the interfering member are engaged, the impact force is passed from the interfering member to the interference member, and when the second impact force is applied to the impacting surface and the interference member and the interfering member are engaged, the resilient material resiliently deforms such that only a portion of the second impact force is passed from the interfering member to the interference member.

21. The method of claim 20, wherein,
the interference member and the interfering member are configured such that when the second impact force is applied to the impacting surface, the resilient material resiliently deforms and allows the interference member and the interfering member to disengage.

* * * * *